(12) United States Patent
Agarwal et al.

(10) Patent No.: US 9,693,775 B2
(45) Date of Patent: Jul. 4, 2017

(54) SURGICAL FASTENER APPLYING APPARATUS

(71) Applicant: Covidien LP, Mansfield, MA (US)

(72) Inventors: Manoj Kumar Agarwal, Jharkhand (IN); Vinayan Vivekanandan, Kerala (IN); Harshotta Singh Dhakad, Madhya Pradesh (IN); Kiran Garikipati, Andhra Pradesh (IN)

(73) Assignee: Covidien LP, Mansfield, MA (US)

( * ) Notice: Subject to any disclaimer, the term of this patent is extended or adjusted under 35 U.S.C. 154(b) by 497 days.

(21) Appl. No.: 14/372,857

(22) PCT Filed: Jan. 9, 2013

(86) PCT No.: PCT/US2013/020840
§ 371 (c)(1),
(2) Date: Jul. 17, 2014

(87) PCT Pub. No.: WO2013/109445
PCT Pub. Date: Jul. 25, 2013

(65) Prior Publication Data
US 2014/0353357 A1 Dec. 4, 2014

Related U.S. Application Data

(60) Provisional application No. 61/587,871, filed on Jan. 18, 2012.

(51) Int. Cl.
*A61B 17/068* (2006.01)
*A61B 17/072* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/115; A61B 17/1155; A61B 17/0686; A61B 2017/07214
USPC .. 227/19, 175.1, 175.2, 175.3, 176.1, 180.1; 606/139, 219
See application file for complete search history.

(56) References Cited

U.S. PATENT DOCUMENTS 6,109,500 A    8/2000  Alli et al.
7,055,730 B2 * 6/2006  Ehrenfels ......... A61B 17/07207
                                              227/175.4

(Continued)

FOREIGN PATENT DOCUMENTS

WO    WO 03/079909 A2   10/2003
WO    WO 03/094745 A1   11/2003

OTHER PUBLICATIONS

Chinese Office Action dated Nov. 7, 2016, issued in Chinese Application No. 201380006087.7.

(Continued)

*Primary Examiner* — Scott A. Smith (57) ABSTRACT

A surgical fastener applying apparatus (10) including a cartridge supporting section (200), an anvil supporting section (100) having a longitudinal axis and including a distal anvil portion (104) and a proximal handle portion (102), including a first longitudinally extending slot (109) extending therealong. A clamping lever (300) having a proximal portion and a distal portion is movable from an unclamped position to a clamped position to releasably secure the anvil supporting section in close approximation with the cartridge supporting section. A firing assembly (500) includes a firing knob (552), the firing knob movable within the longitudinally extending slot from a first proximal position to a second distal position to fire fasteners (402) supported in the cartridge supporting section.

20 Claims, 6 Drawing Sheets

(51) Int. Cl.
  *A61B 17/115* (2006.01)
  *A61B 17/28* (2006.01)
  *A61B 17/00* (2006.01)
  *A61B 90/00* (2016.01)

(52) U.S. Cl.
  CPC ......... *A61B 17/115* (2013.01); *A61B 17/2833* (2013.01); *A61B 2017/0023* (2013.01); *A61B 2017/0053* (2013.01); *A61B 2017/00477* (2013.01); *A61B 2017/07214* (2013.01); *A61B 2017/07271* (2013.01); *A61B 2090/034* (2016.02); *A61B 2090/0811* (2016.02); *A61B 2090/0813* (2016.02)

(56) References Cited

U.S. PATENT DOCUMENTS

| 7,287,682 | B1 | 10/2007 | Ezzat et al. |
| 7,334,717 | B2 * | 2/2008 | Rethy ............... A61B 17/07207 227/175.1 |
| 8,074,861 | B2 * | 12/2011 | Ehrenfels ......... A61B 17/07207 227/175.1 |
| 2004/0007608 | A1 * | 1/2004 | Ehrenfels ......... A61B 17/07207 227/176.1 |
| 2005/0222616 | A1 | 10/2005 | Rethy et al. |
| 2007/0125828 | A1 * | 6/2007 | Rethy .............. A61B 17/07207 227/176.1 |
| 2007/0145095 | A1 * | 6/2007 | Heinrich ............. A61B 17/072 227/175.1 |
| 2011/0084113 | A1 | 4/2011 | Bedi et al. |

OTHER PUBLICATIONS

Chinese Office Action dated Mar. 1, 2016, issued in Chinese Application No. 2013800060877.
International Search Report for PCT/US13/20840 date of completion is Jul. 4, 2013 (6 pages).
European Office Action dated Aug. 19, 2016, issued in EP Application No. 13 701 520.

* cited by examiner

FIG. 9

SURGICAL FASTENER APPLYING APPARATUS

CROSS-REFERENCE TO RELATED APPLICATIONS

This application is a National Stage Application of PCT/US13/20840 under 35 USC §371 (a), which claims priority of U.S. Provisional Patent Application Ser. No. 61/587,871 filed Jan. 18, 2012, the disclosures of each of the above-identified applications are hereby incorporated by reference in their entirety.

BACKGROUND

Technical Field

The present disclosure relates to a surgical fastener applying apparatus and, more particularly, to a surgical fastener applying apparatus having both reusable and disposable components.

Background of Related Art

Surgical fastener applying apparatus grasp or clamp tissue between opposing jaw structures and join the tissue by means of surgical fasteners. In some such apparatus, a knife is provided to cut the tissue which has been joined by the fasteners. The fasteners are typically in the form of surgical staples, although other surgical fasteners may also be utilized, such as, for example, clips or two part polymeric surgical fasteners.

Surgical fastener applying apparatus typically include two elongated beam members which are used to capture or clamp tissue therebetween. Typically, one of the beam members carries a disposable cartridge assembly which houses a plurality of staples arranged in at least two lateral rows, while the other beam member includes an anvil which defines a surface for forming the staple legs as the staples are driven from the cartridge assembly. Where two part fasteners are used, the beam member which includes the anvil carries a mating part of the two part fastener, e.g. the receiver. Generally, the staple formation process is affected by the interaction between one or more longitudinally moving camming members and a series of individual staple pushers. As the camming members travel longitudinally through the cartridge carrying beam member, the individual staple pushers are biased upwardly into a backspan of the staples supported within the cartridge assembly to sequentially eject the staples from the cartridge. A knife may be provided to travel with the camming members between the staple rows to cut the tissue between the rows of formed staples. An example of such an instrument is disclosed in U.S. Pat. No. 7,631,794, which is incorporated herein in its entirety by reference.

Although reusable fastener applying apparatus have been developed, such apparatus can be overly complex and prove difficult to sterilize. Because of the difficulties associated with properly sterilizing a fastener applying apparatus for reuse, fastener applying apparatus are typically configured as disposable apparatus. In such disposable apparatus, the cartridge assembly may be replaced to perform multiple fastener applying operations on a single patient, although the fastener applying apparatus is typically disposed after the surgical procedure has been completed. This need for disposability may increase the costs associated with surgical procedures.

Therefore, a need exists in the art for a fastener applying apparatus which includes reusable components, is not overly complex, and is configured to facilitate proper sterilization after use in a surgical procedure.

SUMMARY

In accordance with one aspect of the present disclosure, a surgical fastener applying apparatus is provided including a cartridge supporting section and an anvil supporting section having a longitudinal axis and including a distal anvil portion and a proximal handle portion. The proximal handle portion has a first surface and a second opposing surface, the first surface facing toward the cartridge supporting section and the second surface including a first longitudinally extending slot extending therealong. A clamping lever has a proximal portion and a distal portion and is movable from an unclamped position to a clamped position to releasably secure the anvil supporting section in close approximation with the cartridge supporting section. A top firing assembly includes a firing knob movable within the longitudinally extending slot from a first proximal position to a second distal position to fire fasteners supported in the cartridge supporting section.

In some embodiments, the clamping lever includes a locking member at the proximal portion wherein the locking member secures the anvil supporting section in a clamped position. The locking member can include a hook. The clamping lever can be biased to an unclamped position by a spring.

In some embodiments, the firing knob is movable to a second proximal position proximal of the first proximal position to release the locking member to release the clamping lever. The longitudinal extending slot can include at least one detent to maintain the firing knob in the first proximal position.

In some embodiments, the firing assembly includes a pair of cam bars operatively connected to the firing knob and the firing knob and cam bars are disposable.

In some embodiments, the first slot has an enlarged width portion at a proximal region thereof and the firing knob is positioned in the enlarged width portion in the first proximal position.

A support block can be provided to support the cam bars which extend distally from the support block and a support post can extend from the support block transverse to the cam bars, to support the firing knob.

In some embodiments, the support block is movable to a proximal position to engage the locking member to unlock the clamping lever.

The cartridge supporting section can include an elongated channel for supporting a disposable loading unit containing a plurality of fasteners.

In some embodiments, a second slot is formed in the anvil in a surface opposite the anvil pockets and extending longitudinally therealong. In some embodiments, the second slot has a first portion with a transverse dimension greater than a second portion, the second portion being closer to the anvil pockets.

In some embodiments, the apparatus further includes an ejector extending from the clamping lever, the ejector movable from a first position to a second position to apply a force against a disposable loading unit positioned in the cartridge supporting section to assist ejection of the disposable loading unit. The cartridge supporting section can include an elongated channel for supporting a disposable loading unit containing a plurality of fasteners and having an opening to receive the ejector therethrough.

In some embodiments, the anvil supporting section includes an indicator adjacent the longitudinally extending slot to indicate the extent of movement of the firing knob.

In accordance with another aspect of the present disclosure, a surgical fastener applying apparatus is provided comprising a cartridge supporting section, an anvil supporting section having a longitudinal axis and including a distal anvil portion and a proximal handle portion, and a clamping lever having a proximal portion and a distal portion. The clamping lever is movable from an unclamped position to a clamped position to releasably secure the anvil supporting section in close approximation with the cartridge supporting section and includes a locking member at the proximal portion securing the anvil supporting section in a clamped position. A firing assembly includes a firing knob movable from a first proximal position to a second distal position to fire fasteners supported in the cartridge supporting section and retractable to a second proximal position proximal of the first proximal position to release the locking member to release the clamping lever.

In some embodiments, the anvil supporting section includes a detent to maintain the firing knob in the first proximal position.

In some embodiments, the firing assembly includes a pair of cam bars operatively connected to the firing knob and the firing knob and the cam bars are disposable.

In some embodiments, a pair of cam bars are operatively connected to the firing knob and a support block supports the cam bars which extend distally from the support block, and a support post extends from the support block transverse to the cam bars, wherein the firing knob extends from the support post and the support block is movable to a proximal position to engage the locking member to unlock the clamping lever.

A spring can be provided to bias the clamping lever to an unclamped position.

The anvil supporting section can include an anvil having a plurality of pockets, the pockets facing the cartridge supporting section, and an elongated slot can be formed in a surface opposite the anvil pockets and extending longitudinally therealong. In some embodiments, the elongated slot has a first portion with a transverse dimension greater than a second portion, the second portion being closer to the anvil pockets.

The apparatus may further include an ejector extending from the clamping lever movable from a first position to a second position to apply a force against a disposable loading unit positioned in the cartridge supporting section to assist ejection of the disposable loading unit. In some embodiments, the cartridge supporting section includes an elongated channel for supporting a disposable unit containing a plurality of fasteners and the elongated channel includes an opening to receive the ejector therethrough.

In accordance with another aspect of the present disclosure, a surgical fastener applying apparatus is provided comprising a cartridge supporting section including an elongated channel for supporting a disposable loading unit containing a plurality of fasteners, an anvil supporting section having a longitudinal axis and including a distal anvil portion and a proximal handle portion and a clamping lever having a proximal portion and a distal portion. The clamping lever is movable from an unclamped position to a clamped position to releasably secure the anvil supporting section in close approximation with the cartridge supporting section. The clamping lever includes an ejector extending therefrom, the ejector movable from a first position to a second position to apply a force against a disposable loading unit positioned in the cartridge supporting section to assist ejection of the disposable loading unit. A firing assembly includes a firing knob movable from a first proximal position to a second distal position to fire fasteners supported in the disposable loading unit.

In some embodiments, pivoting of the clamping lever toward the unclamped position moves the ejector. The elongated channel can include a slot to receive the ejector therethrough.

In some embodiments, the firing assembly includes a pair of cam bars operatively connected to the firing knob and the firing knob and the cam bars are disposable. In such embodiments, the cartridge supporting section, anvil supporting section and clamping lever can be sterilizable and reusable.

A spring can be provided to bias the clamping lever to the unclamped position.

The anvil supporting section can include an anvil having a plurality of pockets facing the cartridge supporting section and an elongated slot formed in a surface opposite the anvil pockets and extending longitudinally therealong. In some embodiments, the anvil slot has a first portion with a transverse dimension greater than a second portion, the second portion being closer to the cartridge supporting section.

BRIEF DESCRIPTION OF THE DRAWINGS

Various embodiments of the presently disclosed surgical fastener applying apparatus are described herein with reference to the drawings wherein.

DETAILED DESCRIPTION

Embodiments of the presently disclosed surgical fastener applying apparatus in accordance with the present disclosure will now be described in detail with reference to FIGS. 1-9, wherein like reference numerals identify similar or identical structural elements. As used herein, as is traditional, the term "proximal" refers to the end of the apparatus which is closer to the user and the term distal refers to the end of the apparatus which is further away from the user.

Figure 1:
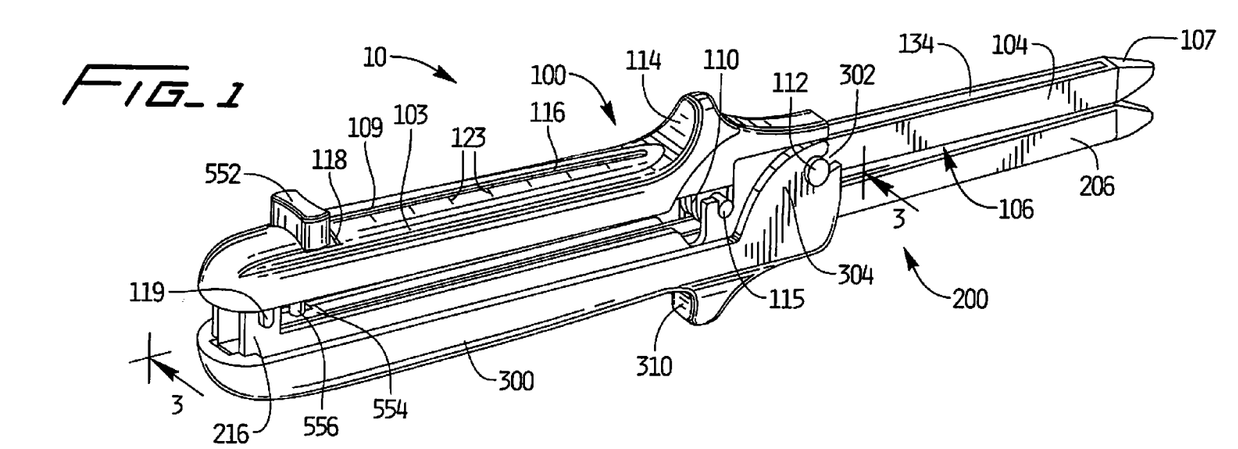
FIG. 1 is a perspective view of the surgical fastener applying apparatus of the present disclosure shown in the clamped position with the firing knob in the pre-fired position.
Figures 2, 2A:
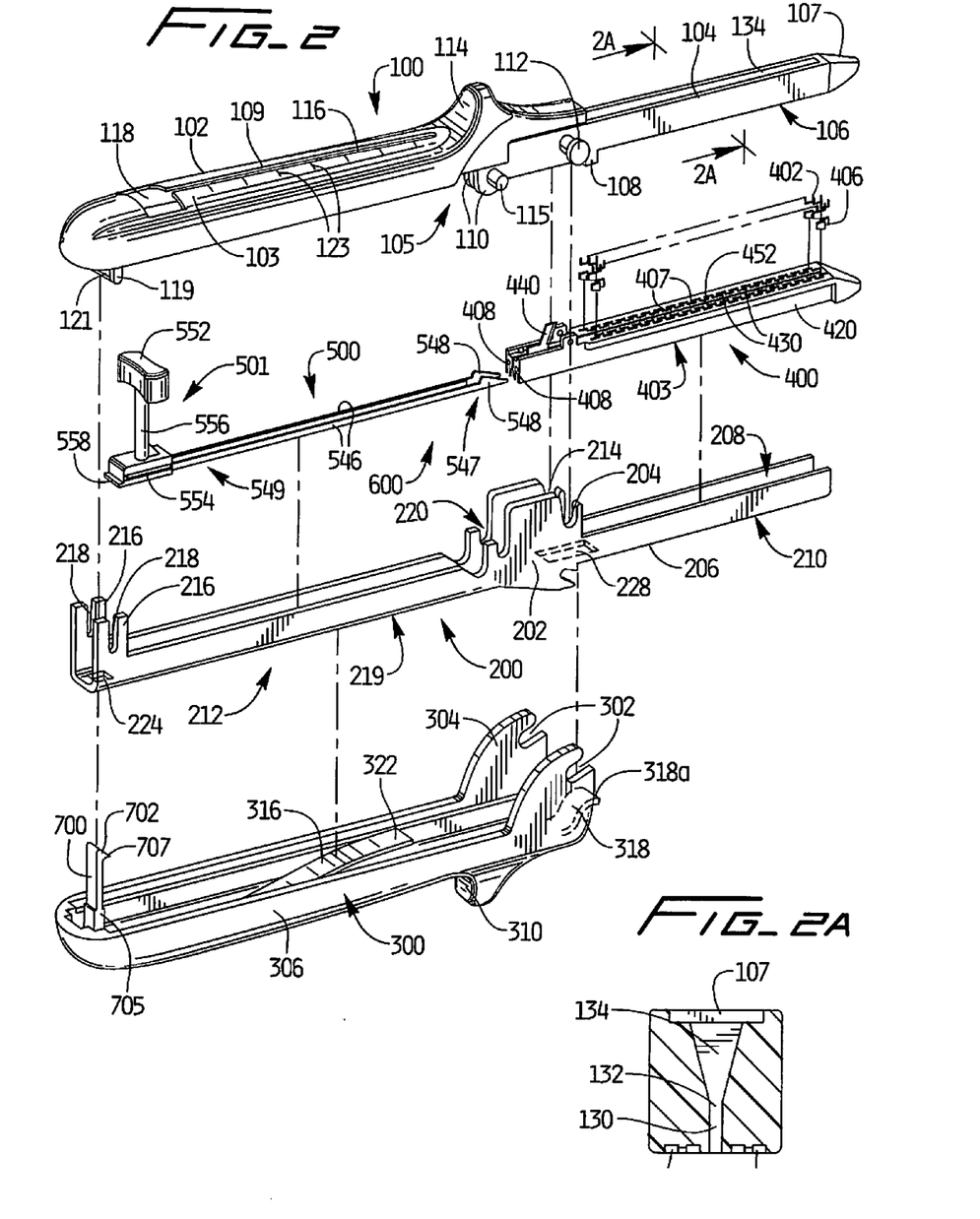
FIG. 2 is a an exploded view of the surgical fastener applying apparatus of FIG. 1.
FIG. 2A is a cross-sectional view taken along line 2A-2A of FIG. 2.
Figure 3:
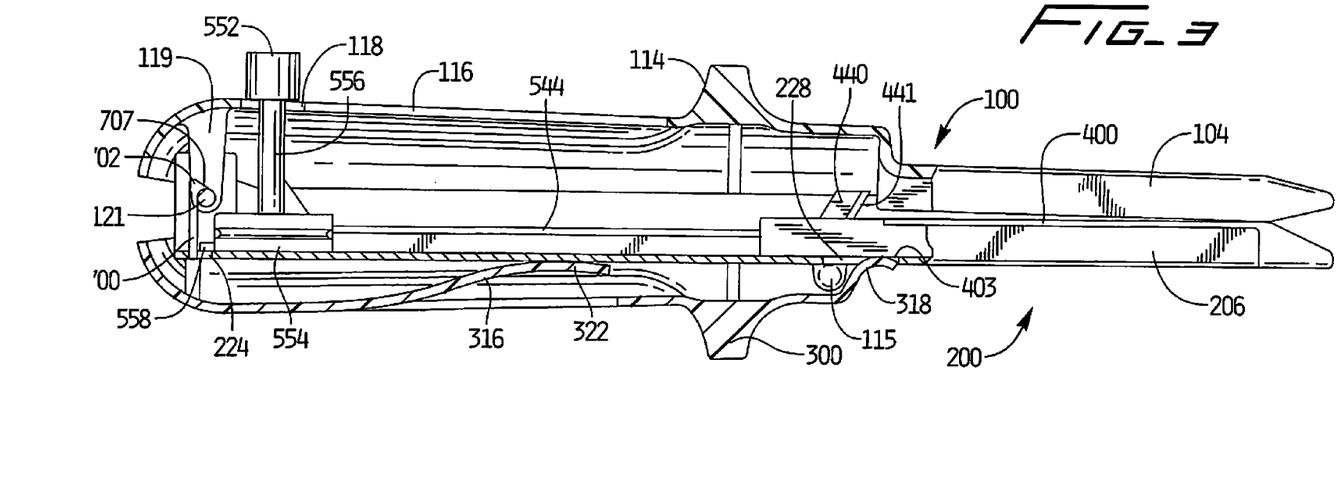
FIG. 3 is a longitudinal cross-sectional view of the surgical fastener applying apparatus taken through line 3-3 of FIG. 1.

Turning to FIGS. 1-3, one embodiment of the presently disclosed surgical fastener applying apparatus is shown generally identified as surgical stapler 10. Surgical stapler 10 includes an anvil supporting or half-section 100, a cartridge supporting or cartridge receiving half-section 200, a clamping lever 300, and a disposable assembly 600 including a single use loading unit 400 (hereinafter "SULU") and a firing unit 500. Each of these components or assemblies will be described in greater detail below.

Figure 9:
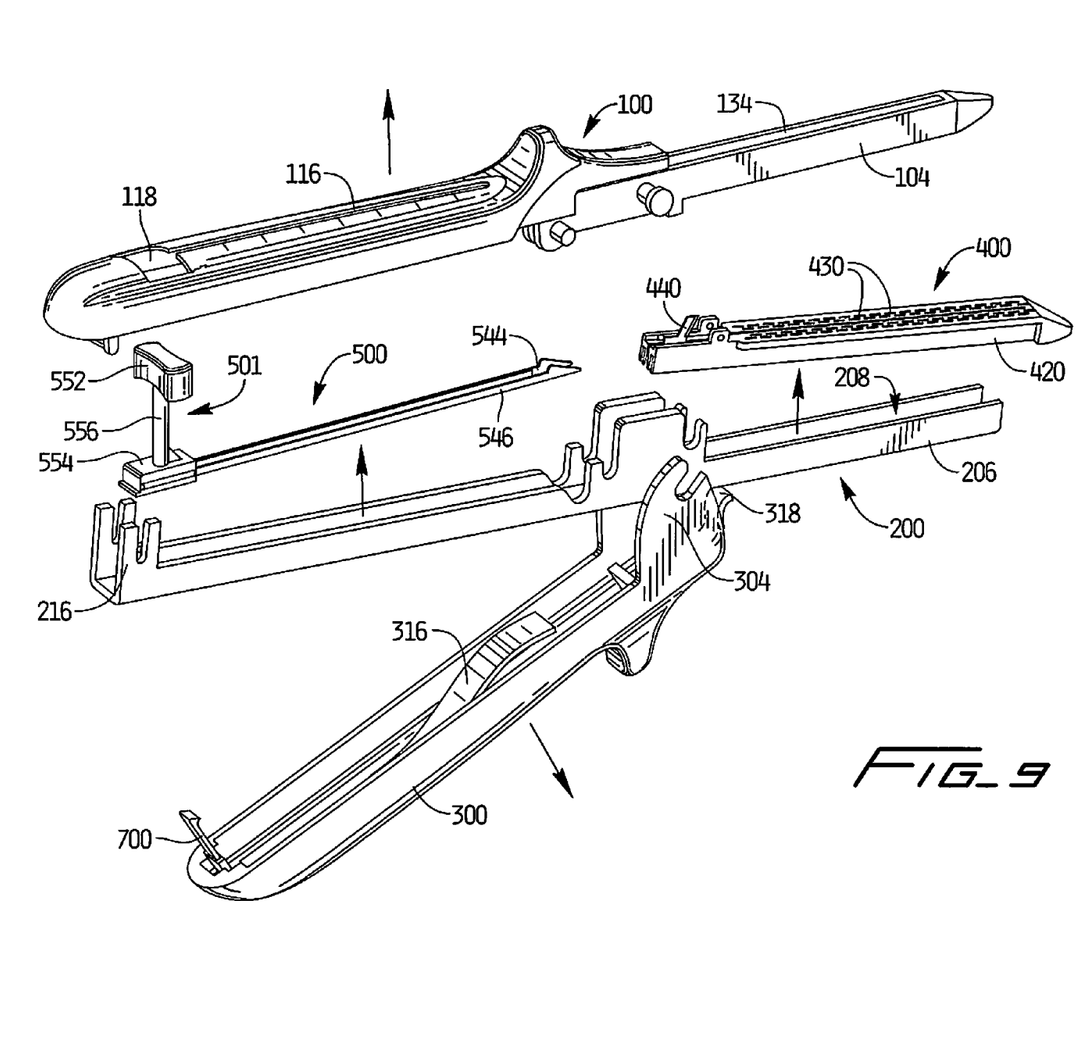
FIG. 9 is a perspective view showing the individual components separated for respective disposal and cleaning.

Anvil half-section 100, cartridge receiving half-section 200 and clamping lever 300 may be configured as reusable components and, as such, are constructed from biocompatible materials suitable for sterilization and repeated use, e.g., stainless steel. SULU 400 and firing unit 500, on the other hand, are disposable. They can be separate components or alternately integrated with one another to form disposable assembly 600. Separation of the components of stapler 10 is illustrated in FIG. 9.

Disposable assembly 600, e.g., SULU 400 and firing unit 500, may be constructed from any suitable biocompatible materials, e.g., plastics, metals, or combinations thereof. Further, surgical stapler 10 may be configured to receive or accommodate disposable assemblies of various different configurations, e.g., disposable assemblies including SULU's and firing assemblies for firing staples of different staple line lengths (e.g., 60 mm, 80 mm and 100 mm).

As will be described in greater detail below, anvil half-section 100 and cartridge-receiving half-section 200 are releasably pivotably engagable with one another, while clamping lever 300 is pivotably coupled to cartridge-receiving half-section 200 about a central portion 202 thereof. Clamping lever 300 is pivotable relative to cartridge-receiving half-section 200 between a spaced-apart position (FIG. 8) and an approximated position (FIGS. 1 and 3) for moving cartridge-receiving half-section 200 and anvil half-section 100 relative to one another between an open, or un-clamped position and a closed, or clamped position (FIGS. 1 and 3) for clamping tissue therebetween. With surgical stapler 10 in the clamped position, firing unit 500 may be operated to sequentially fire and form a plurality of surgical staples 402 (FIG. 2) about tissue clamped between anvil half-section 100 and cartridge-receiving half-section 200 and for advancing a knife 440 to divide tissue between the stapled portions thereof.

Continuing with reference to FIGS. 1-3, anvil half-section 100 includes a proximal handle portion 102 and a distal anvil portion 104 terminating in nose portion 107. Proximal handle portion has an upper surface 103 and an opposing lower surface. Anvil portion 104 includes staple deforming portion 106 which includes a plurality of staple deforming recesses 111 (FIG. 2A) defined therein. Staple deforming portion 106 is disposed in opposing relation relative to SULU 400 when disposable assembly 600 is engaged within channel member 206 of cartridge-receiving half-section 200. Further, staple deforming portion 106 includes a central longitudinal slot 130 (FIG. 2A) for receiving knife 440 of SULU 400 as the knife 440 is advanced through SULU 400 to divide the stapled tissue. Staple deforming portion 106 can be formed integrally with anvil half-section 100 or, alternatively, may be secured to anvil half-section 100 by any suitable fastening process, e.g., welding.

Staple deforming portion 106 is positioned on the side of anvil half-section 100 facing toward the cartridge receiving half-section 200 (and SULU 400). Knife slot 130, as shown in FIG. 2A, extends toward the opposing side of anvil half-section 100. As shown, knife slot 130 has a narrowed region 132 to accommodate sliding movement of the knife 440. Knife slot 130 further progressively increases in width (transverse dimension) away from the cartridge receiving half-section 200 (toward the opposing side of anvil half-section 110) to form a widened slot region 134 to facilitate cleaning of the anvil. Thus, a through slot along the length of the distal anvil portion 106 is provided, tapering inwardly to reduce entry of unwanted debris during the procedure, while providing a progressively increased width to facilitate access for cleaning.

A pair of locating fingers 108 (FIG. 2) disposed on a central portion 105 of anvil half-section 100 and positioned adjacent the proximal end of the staple deforming portion 106 of anvil portion 104 extend from anvil half-section 100 towards SULU 400 of disposable assembly 600. Upon approximation of anvil half-section 100 and cartridge-receiving half-section 200, locating fingers 108 are at least partially received within grooves defined within SULU 400 to properly align SULU 400 with staple deforming portion 106 as surgical stapler 10 is moved to the clamped position.

Anvil half-section 100 further includes a pair of transversely-spaced extensions 110 positioned proximally of fingers 108 which extend downwardly towards disposable assembly 600. The extensions 110 are each also configured to contact an upper surface of a guide block (not shown) as extensions 110 are translated towards disposable assembly 600, i.e., as surgical stapler 10 is moved towards the clamped position, such that the guide block is pivoted from a first, locked position to a second, unlocked position. This guide block and its function and structure are described in detail in commonly assigned U.S. Pat. No. 7,055,730 and application Ser. Nos. 61/494,985, filed Jun. 9, 2011 and 61/521,070, filed Aug. 8, 2011, the entire contents of which are incorporated herein by reference.

A central portion of anvil half-section 100 includes a pair of cylindrical lateral support members 112. During assembly of anvil half-section 100 and cartridge-receiving half-section 200, lateral support members 112 are supported in U-shaped recesses 214 defined in a central portion 202 of cartridge-receiving half-section 200 (FIG. 2). A distal wall 204 of central portion 202 defines a tissue stop. Lateral support members 112 are also positioned to be received in cutouts 302 formed on spaced flange portions 304 of clamping lever 300 when the clamping lever 300 is moved to the clamped position (FIG. 3). Proximal handle portion 102 of anvil half-section 100 is ergonomically formed and includes a thumb-engaging abutment 114. Pins 115 are configured for receipt in slots 220 of cartridge receiving half-section 200.

A proximal end of handle portion 102 includes a downwardly extending pair of arms 119. A transverse post 121 (FIGS. 2 and 3) extends between and is supported by the arms 119. Transverse post 121 is engaged by the locking spring 700 of the clamping lever 300 described below.

A firing slot 109 is provided in the upper surface 103 of handle portion 102 of the anvil section 100. Slot 109 has a longitudinal extending portion 116 and a widened proximal portion 118. Slot 109 is dimensioned to receive the firing knob assembly 501 of firing unit 500 as described below to provide a top firing mechanism for firing fasteners. This top firing mechanism enables easy firing of the stapler 100 with either hand. The elongated width proximal portion 118 can include detents to maintain the firing knob assembly 501 in a prefered position as described below. The detents can be positioned proximal of the firing knob and distal of the firing knob 552 to maintain it in its pre-fired position of FIG. 1.

A series of indicator marks such as markings 123 can be provided adjacent longitudinally extending slot portion 116 to indicate the length of travel of firing knob assembly 501 to thereby indicate staple length applied to tissue.

Cartridge-receiving half-section 200 includes an elongated channel member 206 having a substantially U-shaped channel 208 defined therein that is configured to releasably receive disposable assembly 600. More specifically, U-shaped channel 208 includes a distal portion 210 dimensioned to releasably receive SULU 400 and a proximal portion 212 dimensioned to releasably receive the firing unit 500. A stationary housing can be provided to support the firing unit 500 and SULU 400 which can then be loaded into the channel 208 as one unit. Disposable assembly 600 and the components thereof, i.e., SULU 400 and firing unit 500, will be described in greater detail hereinbelow.

As mentioned above, cartridge-receiving half-section 200 includes spaced centrally disposed U-shaped recesses 214 positioned to support lateral support members 112 of anvil half-section 100. The proximal end of cartridge-receiving half-section 200 includes a pair of vertical support members 216. Each vertical support member 216 includes an elongated vertical slot 218 having a rounded bottom surface. Vertical slots 218 are dimensioned to receive arms 119 of anvil half-section 100 when the anvil half-section 100 is supported on the cartridge-receiving half-section 200 during assembly. By positioning arms 119 within the vertical slots 218, anvil half-section 100 can be pivoted in a scissor-like manner with respect to the cartridge-receiving half-section 200 between the open and closed positions.

As noted above, cartridge-receiving half-section 200 further includes a pair of spaced apart slots 220 configured to receive transversely extending pins 115 of anvil half section 100.

A slot 224 in the bottom wall of channel member 206 in the proximal region of proximal portion 212 is dimensioned to receive therethrough locking spring 700 of clamping lever 300.

Clamping lever 300, as best shown in FIG. 2, includes a handle portion 306 including a thumb engaging abutment 310. A pair of spaced flange portions 304 is supported on the distal end of clamping lever 300. Each flange portion 304 defines a cutout 302 dimensioned to receive a respective lateral support member 112 of anvil half-section 100 when stapler 10 is moved towards the clamped position. A spring member 316 includes a folded-under, T-shaped proximal end that is engaged within opposed slots defined within opposed side walls of clamping lever 300 and may be secured therein in any suitable fashion, e.g., mechanical engagement, welding, adhesion, etc. The distal end 322 of spring member 200 is configured to abut an under surface 219 of cartridge-receiving half-section 200 to bias clamping lever 300 apart from cartridge-receiving half-section 200, i.e., to bias clamping lever 300 towards the spaced-apart, or un-clamped position.

Clamping lever 300 further includes an ejector tab 318 positioned at a distal portion. The ejector 318 is fixedly attached to a bottom surface of the clamping lever 300 and configured to extend through slot 228 formed in the bottom wall of channel member 206. Ejector 318 helps to disengage the SULU 400 from channel 206. Ejector 318 can be in the form of a spring. When clamping lever 300 is pivoted from a clamped position (FIGS. 1-7) to an open position (FIG. 8), the distal end 318a of ejector 318 is pivoted to contact and apply a force to the under surface 403 of the SULU 400 thereby helping to eject the SULU from channel 208.

Locking spring 700 is positioned at a proximal end of clamping lever 300 and includes a distally facing hook 702. Hook 702 is configured to engage substantially cylindrical transverse post 121 of anvil half section 100. That is, when the stapler 10 is clamped, hook 702 is forced past and around, then engages transverse post 121 to hold the clamping lever 300 in the locked (clamped) position as the latching of the hook 702 and post 121 prevents separation of clamping lever 300 and anvil half-section 100.

Figure 7:
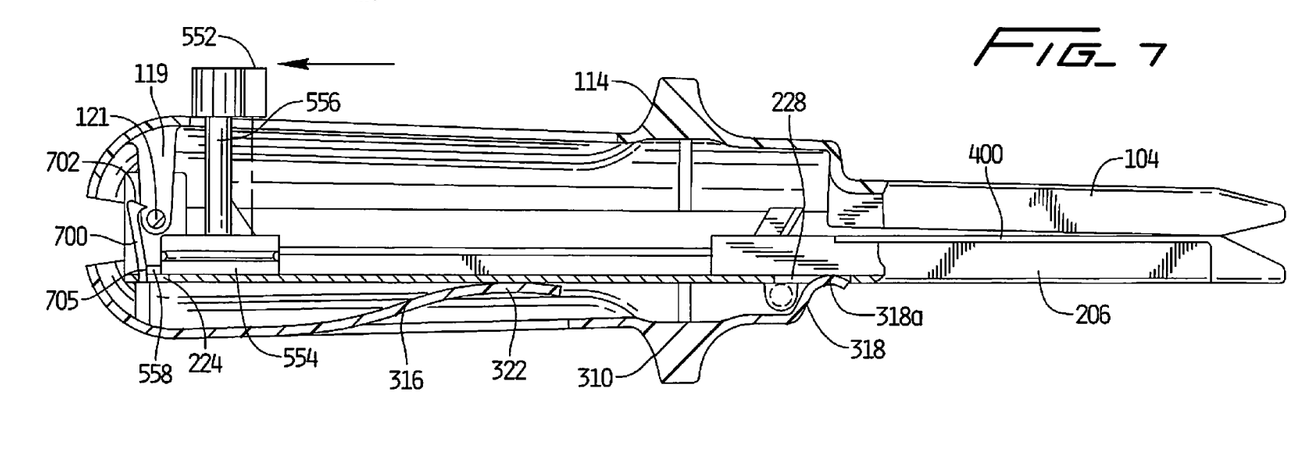
FIG. 7 is a longitudinal cross-sectional view taken along line 7-7 of FIG. 6.
Figure 8:
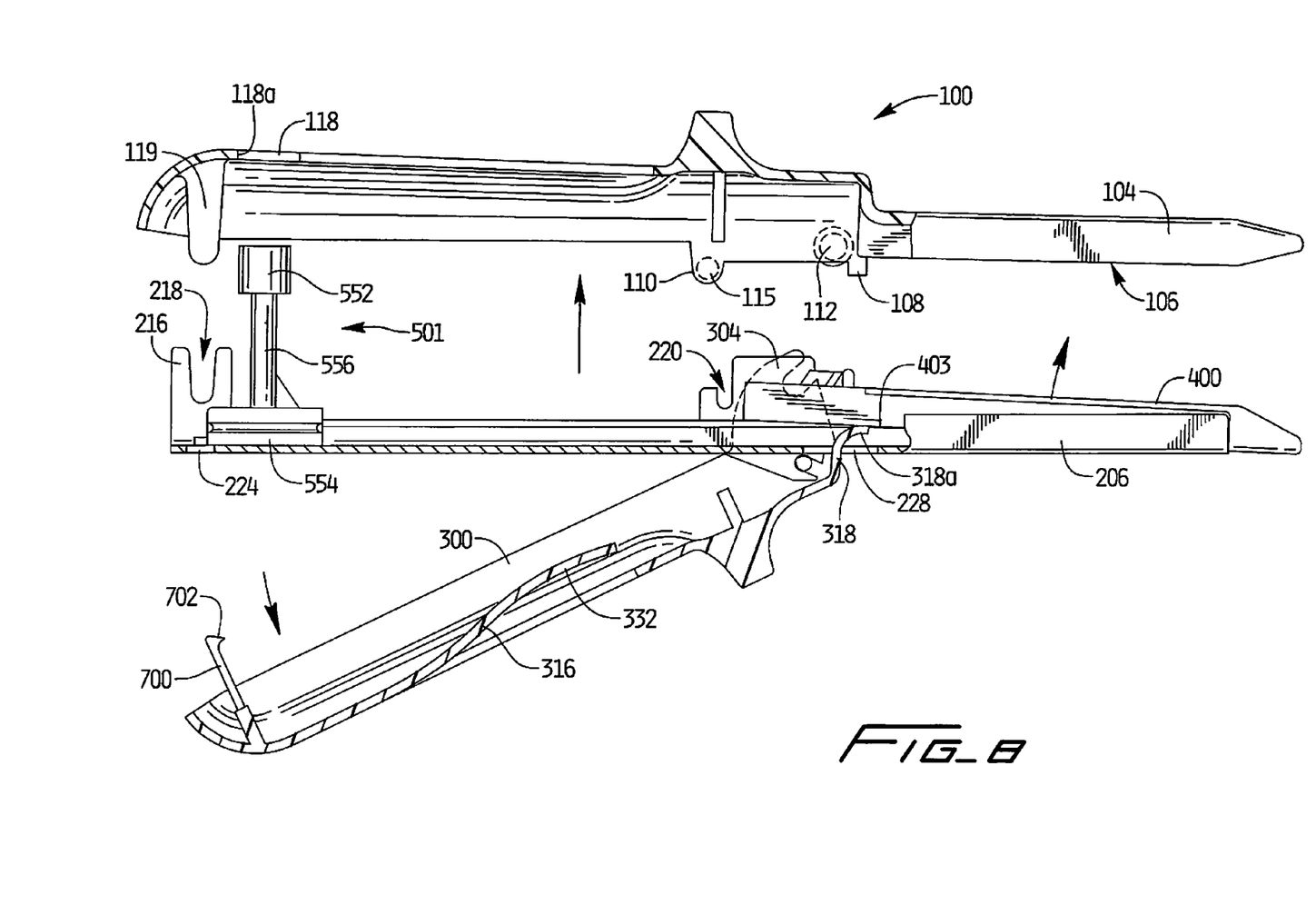
FIG. 8 is a side view of the instrument of FIG. 1 shown in the unclamped position and the anvil and cartridge half-sections separated.

The firing unit 501 disengages the locking spring 702. More specifically, when firing knob 552 is retracted toward its proximalmost position of FIGS. 7 and 8, hook member 702 is disengaged from transverse post 121 to unlock clamping lever 300, thus allowing clamping lever 300 to return under bias of spring 316 back to the open or unclamped position. This disengagement is caused by tab 558 of sliding block 554, extending proximally from sliding block 554 of firing unit 500, engaging a lower portion 705 of spring 700 as shown in FIG. 7 and described below.

As noted above, disposable assembly 600 can include SULU 400 and firing unit 500 integrated with one another to form a single component, i.e., disposable assembly 600. In such single component embodiment, disposable assembly 600 can include a stationary housing (not shown) configured to house the working components of firing unit 500 and a distal extension extending distally from the stationary housing that is configured to engage and retain SULU 400, thus forming an integrated disposable assembly 600. This is shown and described in patent application Ser. No. 61/521,070, filed Aug. 8, 2011, which was previously incorporated herein by reference in its entirety.

Referring to FIGS. 2 and 3 firing unit 500 includes a knife actuating bar 544, a pair of cam bars 546, and a firing knob assembly 501 including a firing knob 552, post 556, and a slide block 554.

The cam bars 546 extend through slots 408 in SULU 400 to fire fasteners 402 housed in SULU 400. That is, as cam bars 546 are moved distally through SULU 400, they contact pushers 406 contained in SULU 400 to sequentially fire the fasteners 402 through the rows of fastener slots 407 in SULU 400.

A guide block such as guide block 48 of patent application Ser. No. 61/494,985 and guide block 548 of application Ser. No. 61/521,070 can be provided having three longitudinal slots; a slot to receive each of the cam bars 546 and another slot to receive the knife actuating bar 544. The guide block, if provided, can be axially fixed within the distal end of a stationary housing and pivotal from the first position in locking engagement with knife actuating bar 544 to the second position disengaged from knife actuating bar 544 in response to movement of stapler 10 to the clamped position. As anvil half-section 100 is approximated relative to cartridge-receiving half-section 200 to achieve the clamped position, extensions 110 of anvil half-section 100 urge the guide block to pivot from the first engaged position to the second disengaged position to disengage the lockout mechanism to enable firing of the fasteners.

Firing knob assembly 501 of instrument 100 is a top firing assembly and includes a finger engagement member or knob 552 which can be selectively engaged by either hand of the user to move the firing unit 500 through a firing stroke. As used herein, a firing stroke is defined as movement of firing knob 552 from a retracted position to a fully advanced position of FIGS. 4 and 5. Firing knob assembly, as noted above, includes a slide block 554 and a post 556 extending upwardly from the slide block 554 substantially perpendicular to the longitudinal axis of the cam bars 546 to connect knob 552 to slide block 554. Post 556 extends through longitudinal slot 109 in anvil section 100. As noted above, a tab 558 extends proximally from the sliding block 554 and is configured to contact and disengage locking spring 700 of clamping lever 300.

Knife actuating bar 544 includes an upturned hook portion and upper and lower notches. A finger projects upwardly from the knife actuating bar 544. When slide block 554 is advanced distally it moves to advance the cam bars 546, and further distal movement effects distal movement of knife actuating bar 544. This arrangement allows for staples to be ejected from SULU 400 prior to cutting of tissue. Details of the knife actuating bar are disclosed in pending application Ser. No. 61/494,985 previously incorporated herein by reference.

Referring to FIG. 2, each cam bar 546 includes distal portion 547, a proximal portion 549 and a pair of sidewalls. The proximal end of each cam bar is fixedly attached to slide block 554. Alternately, slide block 554 may be molded about the proximal end of cam bars 546. In one embodiment, the slide block 554 has a pair of slots to receive the cams bars 546. Due to this attachment, when firing knob 552 is advanced distally, it moves cam bars 546 distally through the slots 408 in the SULU 400 so that angled camming surfaces 548 at the distal portion 547 of cam bars 548 contact pushers 406 to fire the fasteners 402 in a direction substantially perpendicular to the longitudinal axis of the cam bars 546 (substantially perpendicular to the direction of movement of the cam bars 546).

Channel 208 engages and retains SULU 400 therein as wall 206 engages SULU 400 to enclose the underside of cartridge body 420 of SULU 400. Thus, SULU 400 is fixedly secured within channel 206 via a snap-fit engagement. Other securement methods are also contemplated.

Referring to FIG. 2, SULU 400 includes cartridge body 420, a plurality of staple pushers 406, a knife 440 having an angled sharpened leading edge or blade 441, and a plurality of staples 402. A pivotally mounted safety lockout could also be provided as in safety lockout 128 of the 61/494,985 application and safety lockout 428 of application Ser. No. 61/521,070. Body 420 has a plurality of rows of staple retaining slots 430, e.g., four, six, etc. and a linear slotted knife track 452 centrally disposed in body 420. Knife 440 includes a downturned hook portion which is positioned to engage upturned hook portion of knife actuating bar 544 of firing unit 500. In the illustrated embodiment, body 420 includes two staggered rows of slots 430 formed on either side of linear slotted knife track 452. The staggered rows of slots 430 extend beyond the distal end of knife track 452 to facilitate staple formation beyond the distal end of the stroke of the knife blade 440a, although other configurations are contemplated.

Staple pushers 406 may be configured to extend into one or more slots 430. In one embodiment, a single pusher is associated with each slot 430. Alternatively, each pusher 406 can be configured to extend into two adjacent slots 430 and is positioned beneath respective staples 402 which are retained in slots 430. Further, each pusher 406 includes a lower cam surface which is positioned to engage one of cam surfaces 548 on the distal portion 547 of cam bar 546 such that movement of cam bar 546 through SULU 400 sequentially lifts each respective pusher 406 within its respective slot or slots 430 to eject staples from slots 430.

A proximal end of SULU 400 can include opposed, outwardly extending serrated surfaces to facilitate gripping of the proximal end of SULU 400 to facilitate for removal and/or replacement of SULU 400 (or disposable assembly 600) from channel member 206 of cartridge-receiving half-section 200.

A safety lockout 428 of the type described in patent application Ser. No. 61/521,070 and in 61/494,985 (lockout 128) can be provided. When the knife 440 is moved towards the advanced position during a firing stroke, the safety lockout can pivot towards the unlocked position. The safety lockout is prevented from pivoting to the unlocked position when the anvil half-section 100 and cartridge-receiving half-section 200 are in the clamped position because the top surface of the safety lockout engages an inner surface of anvil half-section 100 to prevent pivoting of the safety lockout.

The assembly and operation of surgical stapler 10 will now be described. Initially, disposable assembly 600 is engaged within cartridge-receiving half-section 200. In order to engage disposable assembly 600 within cartridge-receiving half-section 200, disposable assembly 600, which includes SULU 400 and firing unit 500, is generally aligned above cartridge-receiving half-section 200 and is inserted into U-shaped channel 208 of channel member 206 either separately or together if provided as an integrated unit. Installation may be facilitated, as discussed above, by grasping serrated surfaces of SULU 400.

Once disposable assembly 600 is loaded into channel member 206, anvil half-section 100 can be assembled to cartridge-receiving half-section 200. To attach anvil half-section 100 to cartridge-receiving half-section 200, transverse post 121 is positioned in vertical slots 218 of vertical support member 216 of cartridge-receiving half-section 200. Thereafter, anvil half-section 100 is rotated towards cartridge-receiving half-section 200 to position lateral support members 112 in U-shaped recesses 214 of channel member 206. In this position, surgical stapler 10 is ready for use. Note in this position, the firing knob 552 is within the widened slot region 118 of slot 109 of anvil half-section 100, slightly distal of proximal wall 118a.

In use, with surgical stapler 10 in the open, or unclamped position, surgical stapler 10 is manipulated into position such that tissue to be stapled and divided is disposed between anvil half-section 100 and cartridge-receiving half-section 200. Thereafter, surgical stapler 10 may be moved to the clamped position to clamp tissue between SULU 400 and staple deforming portion 106 of anvil half section 100. In order to position surgical stapler 10 in the clamped position, clamping lever 300, which is engaged with cartridge receiving half-section as cutouts 302 receive pins 112 of anvil half-section 100 is rotated in a counter-clockwise direction to the position shown in FIG. 1 after the anvil half section and cartridge receiving half section 200 are attached. As clamping lever 300 is rotated, against the bias of spring member 316, lateral support members 112 are received in cutouts 302 (FIG. 2) of flange portions 304 of clamp lever 300 and are cammed towards cartridge-receiving half-section 200. In this position, as shown in FIG. 1, staple deforming portion 106 is positioned in close approximation with the top surface of SULU 400.

As the clamping lever 300 is moved to the clamped position, angled face 707 of hook 702 of locking spring 700 flexes past transverse post 121 and then returns to its initial position as it passes by post 121 so that hook 702 engages post 121 as shown in FIG. 3. In this clamped position, the engagement of hook 702 with transverse post 121 locks the clamping lever 300 in the clamped or locked position. This latch is released upon proximal movement of firing knob 552 described below.

If a guide block is provided as discussed above, as surgical stapler 10 is moved to the clamped position, extensions 110 of anvil half-section 100 are approximated relative to disposable assembly 600 such that extensions 110 eventually contact the upper surface of guide block and urge the guide block to pivot in a generally counter-clockwise direction so it moves from the locked position to the unlocked position, to unlock the knife actuating bar 544. This prevents movement of the knife actuating bar 544 in relation to the guide block prior to clamping, thus ensuring that the knife actuating bar 544 and knife 440 remain properly positioned for operational engagement prior to use.

When stapler 10 is in the clamped, unfired position, firing unit 500 is in the retracted position at the proximal end of channel member 206, slightly distal of wall 118a. The post 556 of firing knob assembly 501 is in a proximal region 118 of the slot 109. Latch portion (hook) 702 of locking member 700 is engaged with transverse post 121 to retain clamping lever 300 in the clamped position (FIG. 3).

When slide block 554 is in this retracted position, knife 440 and cam surfaces 548 of cam bars 546 are positioned in the proximal end of SULU 400. If a safety lockout is provided, in this position, safety lockout is retained in the locked orientation. In addition, the downturned hook portion of knife 440 is engaged with the upturned hook portion of knife actuating bar 544 to connect firing unit 500 to knife 440 of SULU 400.

Figure 4:
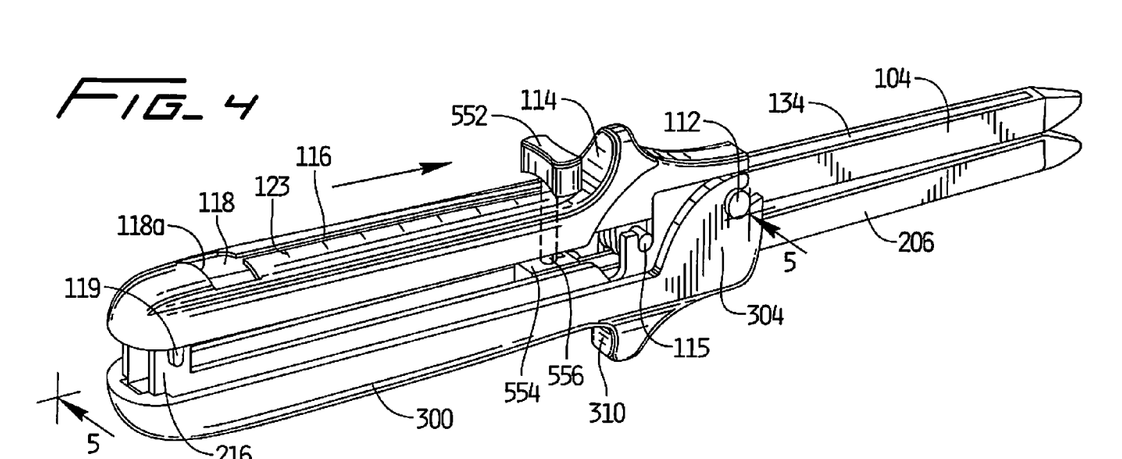
FIG. 4 is a perspective view similar to FIG. 1 showing the firing knob in the advanced position to fire the fasteners.
Figure 5:
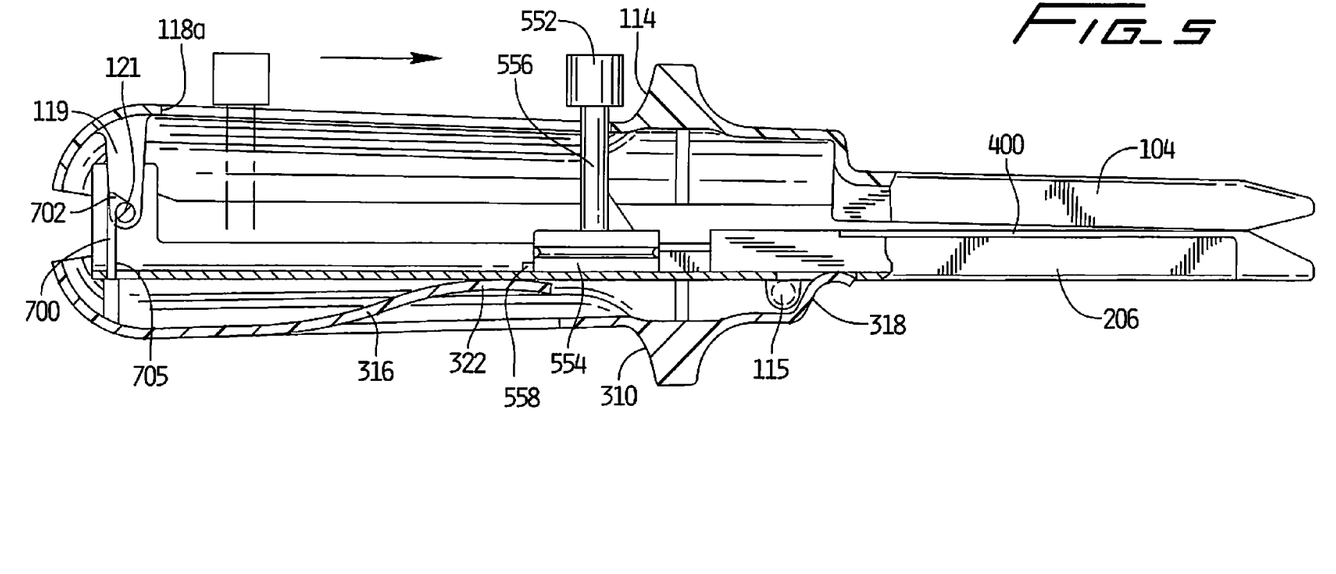
FIG. 5 is a longitudinal cross-sectional view of the surgical fastener applying apparatus taken along line 5-5 of FIG. 4.

When the firing knob 552 is advanced distally to fire the fasteners as shown in FIGS. 4 and 5, slide block 554 is moved distally within channel housing 200, to move cam bars 546 through slots 408 of SULU 400 and to move to knife actuating bar 544 distally. As cam bars 546 are moved distally, cam surfaces 548 sequentially engage pushers 406 to eject staples 402 from slots 407 of body 420. Concurrently, since the distal end of knife actuating bar 544 is engaged with knife 440, knife 440, after the preset delay, is advanced through SULU 400 to incise tissue between the staple lines. Note that as firing knob 552 is moved distally to the position of FIG. 5, the post 556 slides within elongated slot region 116 of slot 109 of anvil half-section 100. Also note that if detents are provided to maintain the firing knob 552 in the position of FIG. 1, a sufficient force needs to be applied to firing knob 552 to override the detents to advance the firing knob 552.

Figure 6:
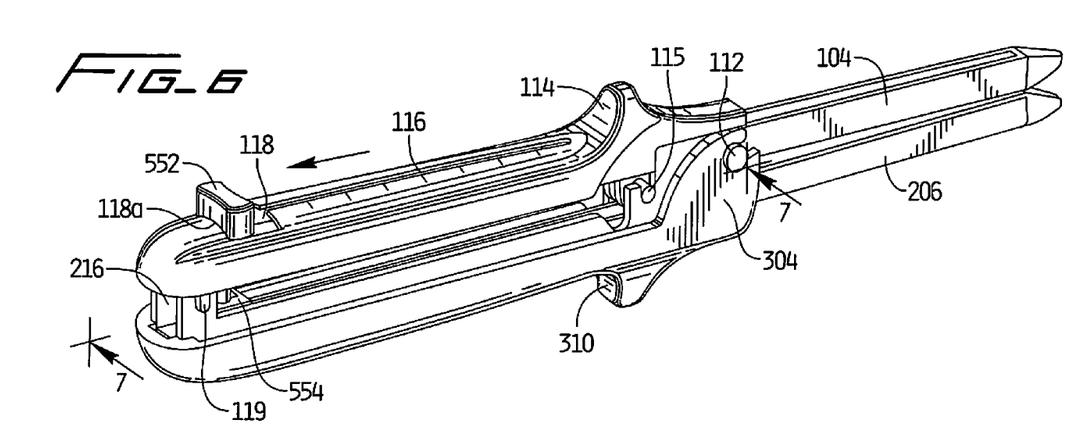
FIG. 6 is a perspective view similar to FIG. 1 showing the firing knob retracted to a proximalmost position to disengage the latch to release the clamping lever.

When the firing knob 552 is returned to its proximal-most position to retract cam bars 546 and knife 440 after firing as shown in FIGS. 6 and 7, post 556 is retracted within elongated slot region 116 of slot 109, and into enlarged region 118. Sufficient proximal retraction of knob 552 causes proximal tab 558 of slide block 554 to engage locking spring 700 to bias it rearwardly as shown in FIG. 7. Note that if proximal detents are provided to retain firing knob 552 in the position of FIG. 1, a sufficient proximal force needs to be applied to firing knob 552 to override the detents to retract the firing knob 552 to its proximalmost position.

Proximal tab 558 bends locking spring so that hook 702 is moved out of engagement with transverse post 121 of anvil half-section 100. This unlocks (unlatches) clamping lever 700 and enables spring 316 to urge clamping lever 300 to its unclamped position to allow stapler 10 to move to the open position. The movement of clamping lever 300 to its open position, moves tab 318a of ejector 318 upwardly through slot 228 of channel member 206 to apply a force to under surface of SULU 400 to aid in its ejection from channel 208 (see FIG. 8). In the open position, anvil half-section 100 is spaced from cartridge-receiving half-section 200 and the components can be separated as in FIG. 8. Note also in this open position, if the aforementioned safety lockout is provided, the safety lockout moves to its unlocked position such that it projects upwardly from SULU 400 to prevent movement of the stapler 10 back to the clamped position. In order to reuse stapler 10, used SULU 400 must be replaced with a new SULU 400.

During a surgical procedure, disposable assembly 600 (including SULU 400 and firing assembly 500) can be replaced multiple times to facilitate multiple uses of stapler 10 on a single patient. Each disposable assembly 600 is provided with a fresh knife. Further, each disposable assembly 600 is also provided with a fresh firing unit 500, e.g., fresh cam bars 546 and firing knob 552, thus inhibiting fatigue or wear of any of the components thereof and simplifying the number and form of components being resterilized. After the surgical procedure, the disposable assembly 600 can be removed from the channel member 206 and disposed of in an appropriate manner.

The anvil half-section 100, cartridge-receiving half-section 200 and clamping lever 300, on the other hand, can be sterilized, such as by autoclaving, and reused with a new disposable assembly 600 in the manner discussed above. Because the firing unit 500 and SULU 400 are all disposable, fewer areas remain on the reusable components for tissue and fluids to become trapped. As such, the reusable components of the apparatus can be more easily sterilized.

It will be understood that various modifications may be made to the embodiments of the surgical fastener applying apparatus disclosed herein. Therefore, the above description should not be construed as limiting, but merely as exemplifications of embodiments. Those skilled in the art will envision other modifications within the scope and spirit of the present disclosure.

What is claimed is:

1. A surgical fastener applying apparatus comprising:
a cartridge supporting section;
an anvil supporting section having a longitudinal axis and including a distal anvil portion and a proximal handle portion, the proximal handle portion having a first surface and a second opposing surface, the first surface facing toward the cartridge supporting section, the second surface including a first longitudinally extending slot extending therealong;
a clamping lever having a proximal portion and a distal portion, the clamping lever movable from an unclamped position to a clamped position to releasably secure the anvil supporting section in close approximation with the cartridge supporting section; and
a top firing assembly including a firing knob, the firing knob movable within the longitudinally extending slot from a first proximal position to a second distal position to fire fasteners supported in the cartridge supporting section.

2. The surgical fastener applying apparatus according to claim 1, wherein the clamping lever includes a locking member at the proximal portion, the locking member securing the anvil supporting section in a clamped position.

3. The surgical fastener applying apparatus according to claim 2, the firing knob is movable to a second proximal position proximal of the first proximal position to release the locking member to release the clamping lever.

4. The surgical fastener applying apparatus according to claim 3, wherein the locking member includes a hook.

5. The surgical fastener applying apparatus according to claim 1, wherein the first longitudinally extending slot includes at least one detent to maintain the firing knob in the first proximal position.

6. The surgical fastener applying apparatus according to claim 1, wherein the firing knob is disposable.

7. The surgical fastener applying apparatus according to claim 1, wherein the firing assembly includes a pair of cam bars operatively connected to the firing knob, the cam bars being disposable.

8. The surgical fastener applying apparatus according to claim 7, further comprising a support block supporting the cam bars, the cam bars extending distally from the support block and a support post extending from the support block transverse to the cam bars, the firing knob extending from the support post.

9. The surgical fastener applying apparatus according to claim 8, wherein the clamping lever includes a locking member at the proximal portion, the locking member securing the anvil supporting section in a clamped position, the support block movable to a proximal position to engage the locking member to unlock the clamping lever.

10. The surgical fastener applying apparatus according to claim 1, wherein the first slot has an enlarged width portion at a proximal region thereof, the firing knob positioned in the enlarged width portion in the first proximal position.

11. The surgical fastener applying apparatus according to claim 1, wherein the cartridge supporting section includes an elongated channel for supporting a disposable loading unit containing a plurality of fasteners.

12. The surgical fastener applying apparatus according to claim 1, further comprising a spring biasing the clamping lever to an unclamped position.

13. The surgical fastener applying apparatus according to claim 1, wherein the anvil supporting section includes an anvil having a plurality of pockets, the pockets facing the cartridge supporting section, and a second slot formed in a surface opposite the anvil pockets and extending longitudinally therealong.

14. The surgical fastener applying apparatus according to claim 13, wherein the second slot has a first portion with a transverse dimension greater than a second portion, the second portion being closer to the anvil pockets.

15. The surgical fastener applying apparatus according to claim 1, further comprising an ejector extending from the clamping lever, the ejector movable from a first position to a second position to apply a force against a disposable loading unit positioned in the cartridge supporting section to assist ejection of the disposable loading unit.

16. The surgical fastener applying apparatus according to claim 1, wherein the cartridge supporting section includes an elongated channel for supporting a disposable loading unit containing a plurality of fasteners, the elongated channel includes an opening to receive an ejector therethrough.

17. The surgical fastener applying apparatus according to claim 1, wherein the anvil supporting section includes an indicator adjacent the longitudinally extending slot to indicate the extent of movement of the firing knob.

18. A surgical fastener applying apparatus comprising:
a cartridge supporting section;
an anvil supporting section having a longitudinal axis and including a distal anvil portion and a proximal handle portion;
a clamping lever having a proximal portion and a distal portion, the clamping lever movable from an unclamped position to a clamped position to releasably secure the anvil supporting section in close approximation with the cartridge supporting section, the clamping lever including a locking member at the proximal portion, the locking member securing the anvil supporting section in a clamped position; and
a firing assembly including a firing knob, the firing knob movable from a first proximal position to a second distal position to fire fasteners supported in the cartridge supporting section and retractable to a second proximal position proximal of the first proximal position to release the locking member to release the clamping lever.

19. The surgical fastener applying apparatus according to claim 18, wherein the anvil supporting section includes a detent to maintain the firing knob in the first proximal position.

20. The surgical fastener applying apparatus according to claim 18, wherein the firing assembly includes a pair of cam bars operatively connected to the firing knob, the firing knob and the cam bars being disposable.

* * * * *

UNITED STATES PATENT AND TRADEMARK OFFICE
CERTIFICATE OF CORRECTION

PATENT NO. : 9,693,775 B2
APPLICATION NO. : 14/372857
DATED : July 4, 2017
INVENTOR(S) : Manoj Kumar Agarwal et al.

It is certified that error appears in the above-identified patent and that said Letters Patent is hereby corrected as shown below:

The Inventors should read:

(72) Inventors: Manoj Kumar Agarwal, Jharkhand (IN);
Vinayan Vivekanandan, Kerala (IN);
Harshottam Singh Dhakad, Madhya Pradesh (IN);
Kiran Garikipati, Andhra Pradesh (IN)

Signed and Sealed this
Seventh Day of November, 2017

Joseph Matal
*Performing the Functions and Duties of the*
*Under Secretary of Commerce for Intellectual Property and*
*Director of the United States Patent and Trademark Office*